United States Patent
Gobber et al.

(10) Patent No.: US 11,571,487 B2
(45) Date of Patent: Feb. 7, 2023

(54) REFILL FOR DEVICES FOR EVAPORATING VOLATILE SUBSTANCES

(71) Applicant: Zobele Holding S.P.A., Trento (IT)

(72) Inventors: Cedric Gobber, Barcelona (ES); Moisés Caballero Tapia, Barcelona (ES); Jordi Masó Sabaté, Barcelona (ES)

(73) Assignee: ZOBELE HOLDING S.P.A., Trento (IT)

( * ) Notice: Subject to any disclaimer, the term of this patent is extended or adjusted under 35 U.S.C. 154(b) by 694 days.

(21) Appl. No.: 16/475,786

(22) PCT Filed: Dec. 19, 2017

(86) PCT No.: PCT/EP2017/083515
§ 371 (c)(1),
(2) Date: Jul. 3, 2019

(87) PCT Pub. No.: WO2018/127402
PCT Pub. Date: Jul. 12, 2018

(65) Prior Publication Data
US 2021/0145999 A1    May 20, 2021

(30) Foreign Application Priority Data
Jan. 5, 2017   (ES) .................. P201730008

(51) Int. Cl.
*A61L 9/12*   (2006.01)
*B05B 11/00*   (2006.01)

(52) U.S. Cl.
CPC ......... *A61L 9/127* (2013.01); *A61L 2209/133* (2013.01); *B05B 11/0038* (2018.08)

(58) Field of Classification Search
CPC . A61L 9/127; A61L 2209/133; B05B 11/0038
USPC .................................................. 392/390, 395
See application file for complete search history.

(56) References Cited

U.S. PATENT DOCUMENTS

| | | | |
|---|---|---|---|
| 6,659,301 B2 * | 12/2003 | Fellows ................. | A61L 9/037 215/400 |
| 9,370,594 B2 * | 6/2016 | Gasper .................... | A61L 9/037 |
| 9,669,125 B2 * | 6/2017 | Gasper .................... | A61L 9/035 |
| 10,258,710 B1 * | 4/2019 | Pieper .................... | A61M 21/00 |
| 10,973,944 B1 * | 4/2021 | Farrell .................... | A61L 9/14 |
| 2003/0189022 A1 | 10/2003 | Fellows | |
| 2006/0219800 A1 | 10/2006 | Junwu | |
| 2021/0213152 A1 * | 7/2021 | Richard ................. | A61L 9/037 |

OTHER PUBLICATIONS

International Search Report dated Apr. 9, 2018 in co-pending International Application No. PCT/EP2017/083515.

* cited by examiner

*Primary Examiner* — Timothy L Maust
(74) *Attorney, Agent, or Firm* — Sandberg Phoenix & von Gontard PC

(57) ABSTRACT

A refill for devices for evaporating volatile substances includes a body (1) provided with a neck (2). The body has a first coupling means (4; 5; 6) for coupling the body to a device (10; 20; 30) for evaporating volatile substances and also at least a second coupling means (4; 5; 6) for coupling the body to a device for evaporating volatile substances (10; 20; 30).
The refill can be used with different devices for evaporating volatile substances by using one of said coupling means, depending on the means provided in the device.

20 Claims, 4 Drawing Sheets

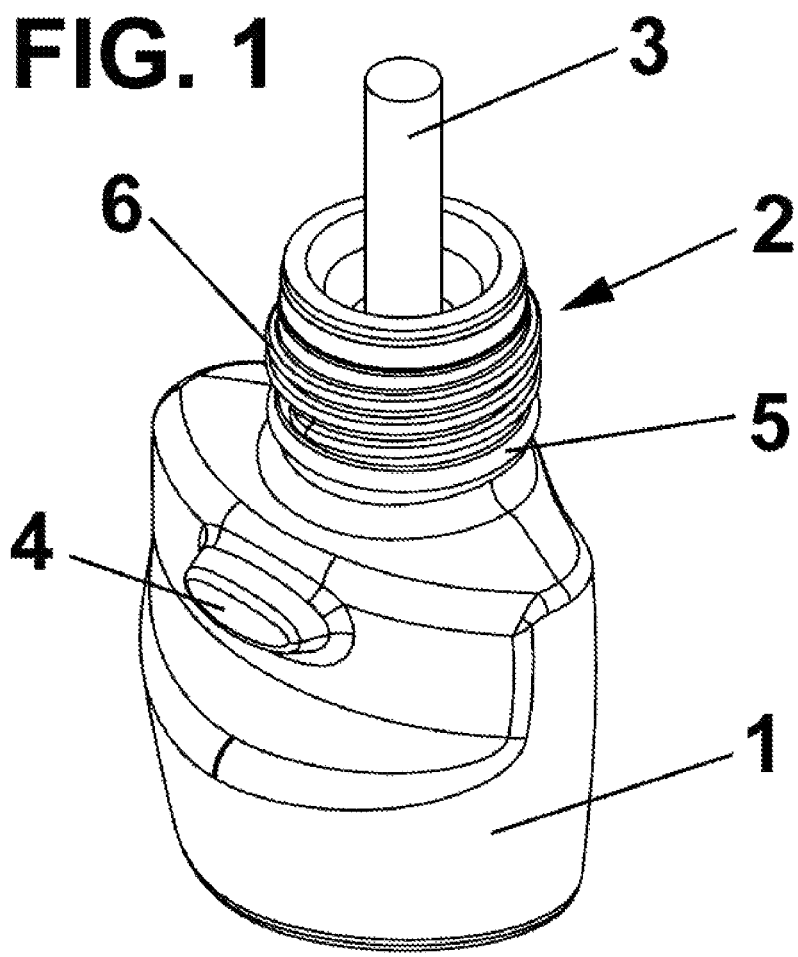

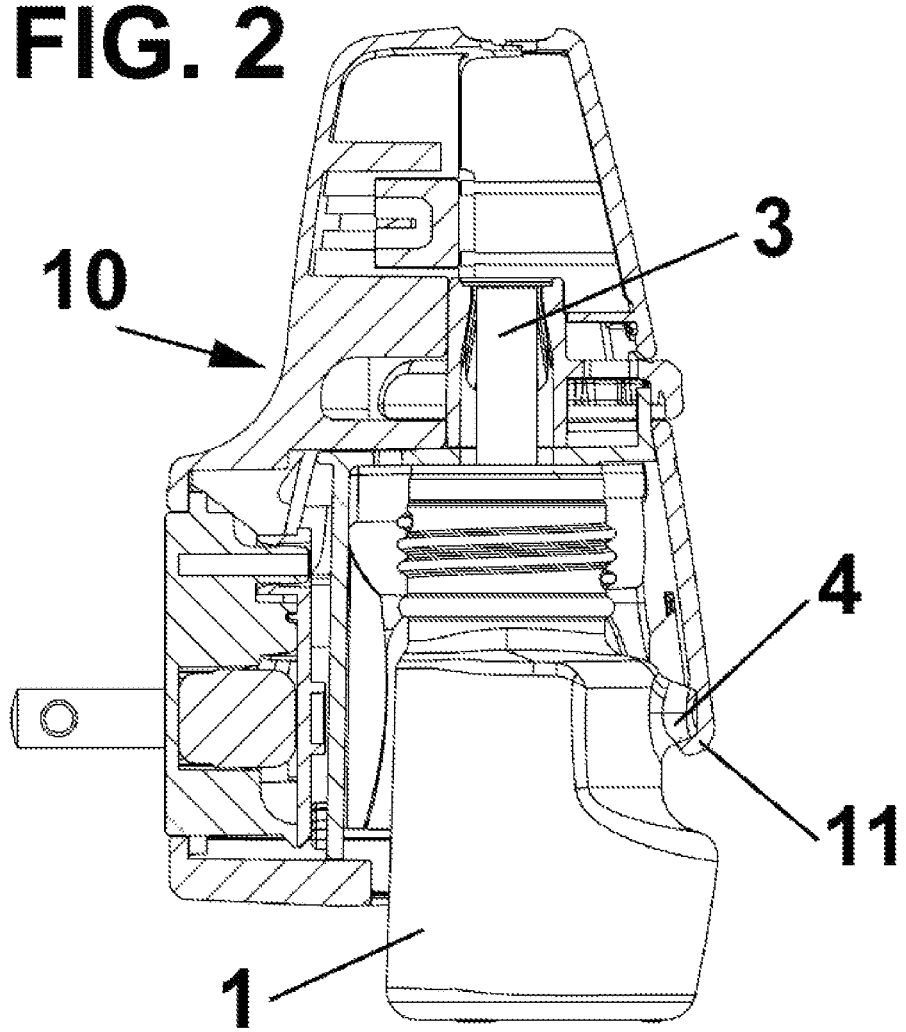

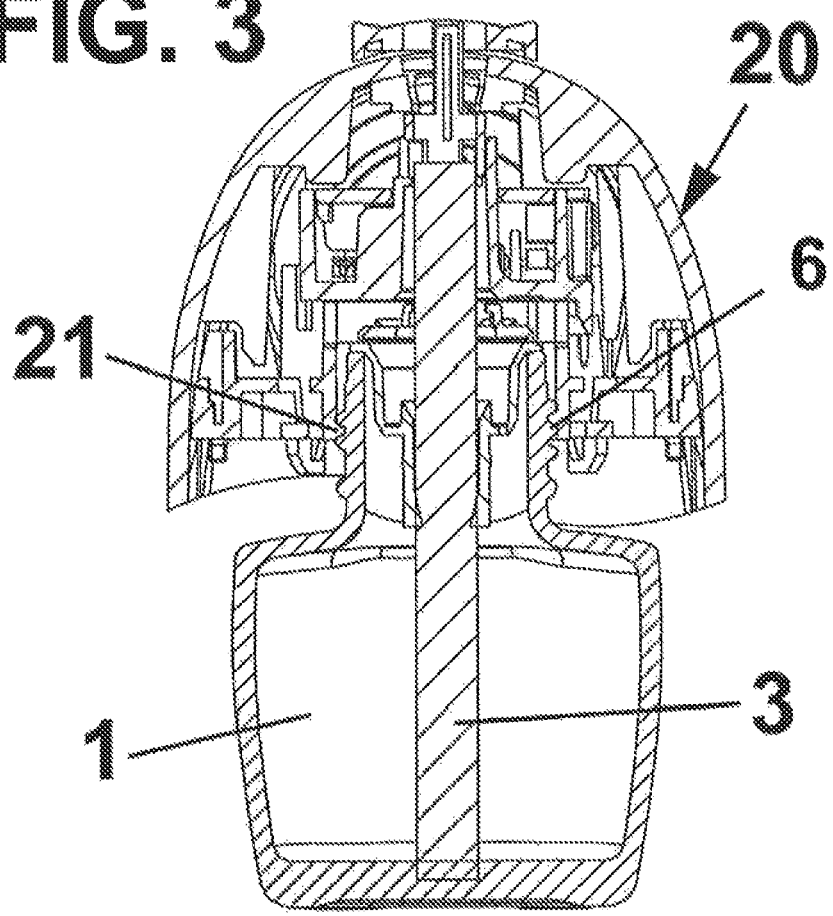

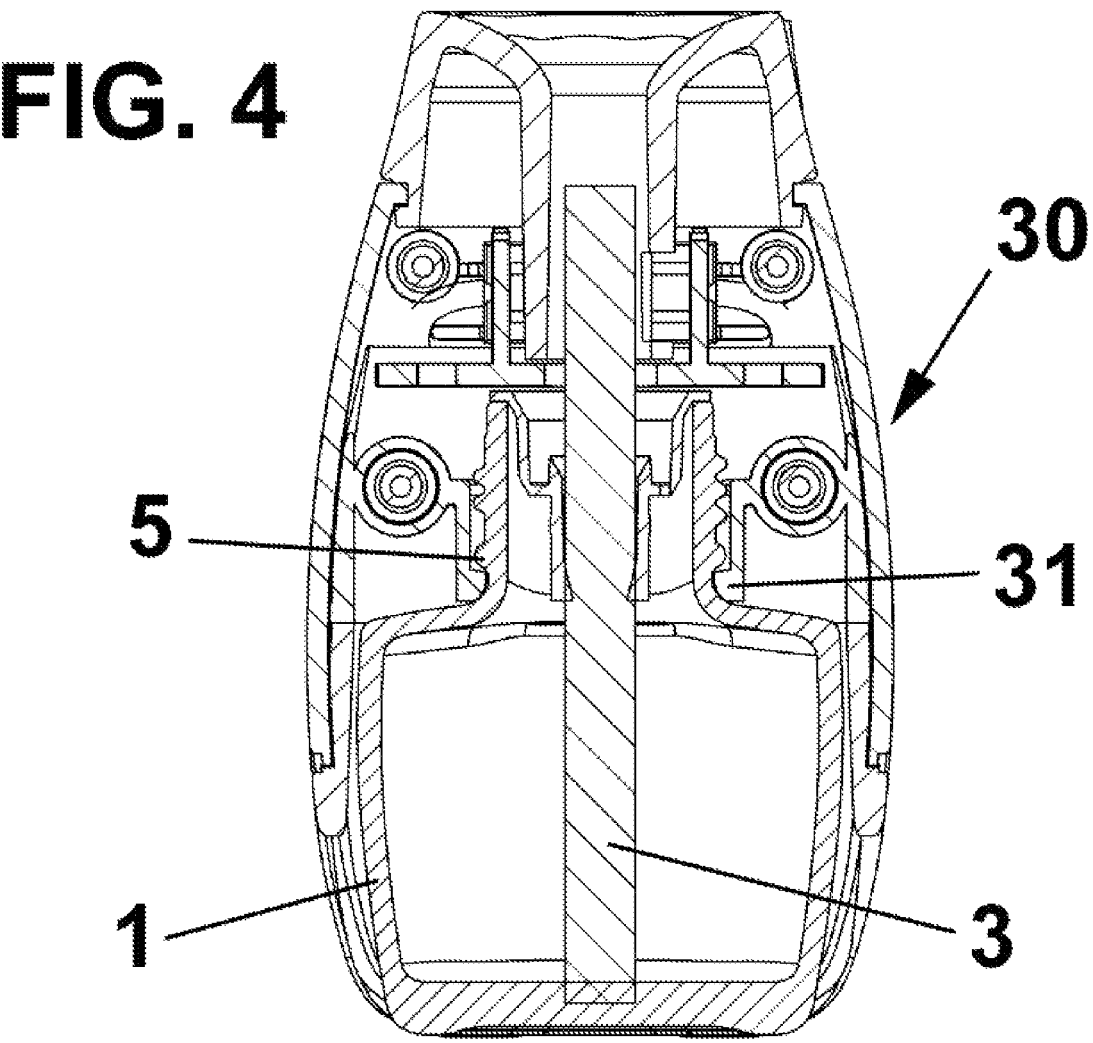

REFILL FOR DEVICES FOR EVAPORATING VOLATILE SUBSTANCES

CROSS REFERENCE TO RELATED APPLICATION

This application is a U.S. national stage application filed under 35 U.S.C. § 371 of International Patent Application No. PCT/EP2017/083515 filed on Dec. 19, 2017, which international application claims priority to Spanish national patent application No. P201730008 filed on Jan. 5, 2017. The foregoing applications are incorporated by reference herein in their entirety.

STATEMENT REGARDING FEDERALLY SPONSORED RESEARCH OR DEVELOPMENT

Not applicable.

SEQUENCE LISTING, TABLE OR COMPUTER PROGRAM ON COMPACT DISC

Not applicable.

FIELD OF INVENTION

The present invention relates to a refill for devices for evaporating volatile substances, which enables the assembly thereof in different types of evaporating devices.

BACKGROUND OF THE INVENTION

The use of devices for evaporating volatile substances such as air fresheners or insecticides is common. These evaporating devices can be connected to the electrical grid in order to cause the volatile substance to evaporate.

The volatile product that evaporates is housed in a refill coupled to the evaporating device, such that when said volatile product runs out, the refill is removed and is replaced by another refill.

The coupling of the refill with the evaporating device can be carried out in different ways, for example, by means of a thread, so that the user can easily couple and remove the refill.

A drawback of these refills is that they are specially designed for use in a single evaporating device, comprising a single coupling means to the evaporating device for which it is designed. In this way, the user is forced to remember what type of evaporating device they have in order to purchase the suitable refill for that evaporating device, since, if they buy another type of refill, they will not be able to use it with that evaporating device.

This drawback for users also has consequences for refill manufacturers, since they have to manufacture different types of refills, one for each type of evaporating device, with the subsequent manufacturing and storage costs for all these types of refills.

Therefore, an objective of the present invention is providing a refill for devices for evaporating volatile substances that enables the use thereof in more than one type of evaporating device, by providing at least two different coupling means to be able to couple to at least two different types of evaporating devices.

SUMMARY OF THE INVENTION

The refill according to the present invention solves the aforementioned drawbacks and has other advantages, which are described below.

The refill for devices for evaporating volatile substances according to the present invention comprises a body provided with a neck, which comprises first coupling means or a first coupler to a device for evaporating volatile substances, and is characterized in that it also comprises at least second coupling means or a second coupler to a device for evaporating volatile substances.

Advantageously, the refill for devices for evaporating volatile substances according to the present invention also comprises third coupling means or a third coupler to a device for evaporating volatile substances.

According to a preferred embodiment, said first coupling means is a thread arranged in said neck of the refill, said second coupling means is a projection arranged in said body of the refill, and said third coupling means is a ring-shaped flange arranged in said neck.

Furthermore, preferably, said ring-shaped flange is arranged underneath said thread.

The refill according to the present invention has the advantage that it can be used with different devices for evaporating volatile substances by using one of said coupling means, depending on the means provided in the device.

This represents an obvious advantage for the manufacturer of the refill, as it substantially reduces manufacturing and storage costs, by manufacturing and storing a single refill that can be used with two or three different types of evaporating devices.

BRIEF DESCRIPTION OF THE DRAWINGS

For the purpose of helping to make the foregoing description more readily understandable, it is accompanied by a set of drawings which, schematically and by way of illustration and not limitation, represent a practical embodiment.

FIG. 1 is a perspective view of the refill for devices for evaporating volatile substances according to the present invention;

FIG. 2 is a cross-sectional view of the refill for devices for evaporating volatile substances according to the present invention mounted on an evaporating device using a projection;

FIG. 3 is a cross-sectional view of the refill for devices for evaporating volatile substances according to the present invention mounted on an evaporating device using a thread; and FIG. 4 is a cross-sectional view of the refill for devices for evaporating volatile substances according to the present invention mounted on an evaporating device using a ring-shaped flange.

DETAILED DESCRIPTION

As shown in FIG. 1, the refill according to the present invention comprises a body 1 provided with a neck 2. Inside said body 1 a volatile product is housed, for example, an air freshener or insecticide product, which impregnates a wick 3 that projects from said body 1, through which the evaporation of the volatile substances of the product occurs when the refill is coupled to an evaporating device.

According to the present invention, the refill comprises more than a one coupling means or more than one coupler for coupling the refill to a device for evaporating volatile substances. The refill is adapted to be releasably attached to a plurality of different devices for evaporating volatile substances that are separate from the refill.

According to the represented embodiment, the coupling means are a projection 4 arranged in said body 1, a ring-shaped flange 5 arranged in said neck 2 and a thread 6 arranged in said neck 2, which can be used independently from each other in order to be coupled to different evaporating devices.

As can be seen in FIG. 1, in order to enable the use of the ring-shaped flange 5 or of the thread 6 indistinctly, said ring-shaped flange 5 is arranged under the thread 6 in the neck 2 of the refill, and said ring-shaped flange 5 protruding more than said thread 6.

It should be noted that said coupling means are only examples for coupling to the most common evaporating devices. Furthermore, it is not essential that the refill have three coupling means, since it could have two of said coupling means or more than three.

FIGS. 2 and 4 show how said coupling means or couplers are used in different evaporating devices.

FIG. 2 shows an evaporating device, generally identified by reference number 10 with the refill coupled therein, in this case by means of the projection 4 described above.

In this case, the projection 4 arranged in the body 1 of the refill is snap-fitted with a tab 11 of said evaporating device 10. In this way, the refill is placed by simply pushing it towards the inside of the housing thereof in the evaporating device until the projection 4 is snap-fitted inside the tab 11, and it can be removed by carrying out the inverse movement.

FIG. 3 shows another evaporating device, generally identified by reference number 20 with the refill coupled therein, in this case by means of the thread 6 described above.

In this case, the thread 6 of the refill is coupled in a complementary thread 21 of said evaporating device 20. The refill is placed simply by screwing it in by means of said threads 6, 21 and is removed by unscrewing it, FIG. 4 shows another evaporating device, generally identified by reference number 30 with the refill coupled therein, in this case by means of the ring-shaped flange 5 described above.

In this case, the ring-shaped flange 5 is snap-fitted with a ring 31 of the evaporating device 30. Thus, the refill is placed by simply pushing it towards the inside of the housing thereof in the evaporating device until the ring-shaped flange 5 is snap-fitted into the ring 31, and it can be removed by carrying out the inverse movement.

Although reference has been made to a specific embodiment of the invention, it is evident for a person skilled in the art that numerous variations and modifications can be made to the refill for devices for evaporating volatile substances described above, and that all the aforementioned details can be replaced by other technically equivalent ones, without departing from the scope of protection defined by the attached claims.

The invention claimed is:

1. A refill adapted to be releasably attached to a plurality of different devices for evaporating volatile substances that are separate from the refill, the refill comprising:
   a body;
   a neck on the body;
   a first coupler on the refill, the first coupler having a means for attaching the refill to a first device for evaporating volatile substances that is separate from the refill;
   a second coupler on the refill, the second coupler having a means for attaching the refill to a second device for evaporating volatile substances that is separate from the refill; and
   a third coupler on the refill, the third coupler having a means for attaching the refill to a third device for evaporating volatile substances that is separate from the refill.

2. The refill of claim 1, further comprising:
   the first coupler, the second coupler and the third coupler are separate and have different configurations.

3. The refill of claim 1, further comprising:
   the means for attaching the refill to the first device, the means for attaching the refill to the second device and the means for attaching the refill to the third device for evaporating volatile substances are different means for attaching the refill to devices for evaporating volatile substances.

4. The refill of claim 1, further comprising:
   the first coupler is positioned on the neck, the second coupler is positioned on the body and the third coupler is positioned on the neck enabling the first coupler, the second coupler and the third coupler to be used independently from each other to couple the refill to different devices for evaporating volatile substances.

5. The refill of claim 1, further comprising:
   a wick projects from the body, the wick enables evaporation of volatile substances in the body through the wick.

6. The refill of claim 1, further comprising:
   the first coupler is a thread on the neck;
   the second coupler is a projection on the body; and
   the third coupler is a ring-shaped flange on the neck.

7. The refill of claimed 6, further comprising:
   the thread on the neck, the projection on the body and the ring-shaped flange on the neck are usable independently of each other to couple the refill to different devices for evaporating volatile substances.

8. The refill of claim 6, further comprising:
   the ring-shaped flange on the neck is positioned underneath the thread on the neck enabling use of the ring-shaped flange or the thread distinctly to couple the refill to a device for evaporating volatile substances.

9. The refill of claim 6, further comprising:
   the thread on the neck is configured to be coupled to a complementary thread of a device for evaporating volatile substances to couple the refill to the device for evaporating volatile substances by screwing the thread to the complementary thread of the device for evaporating volatile substances;
   the projection on the body is configured to be snap fit to a tab of a device for evaporating volatile substances to couple the refill to the device for evaporating volatile substances by pushing the refill onto the device for evaporating volatile substances; and
   the ring-shaped flange on the neck is configured to be snap fit to a tab of a device for evaporating volatile substances to couple the refill to the device for evaporating volatile substances by pushing the refill onto the device for evaporating volatile substances.

10. The refill of claim 9, further comprising:
    the thread on the neck is configured to be decoupled from the complementary thread of the device for evaporating volatile substances to separate the refill from the device for evaporating volatile substances by unscrewing the thread from the complementary thread of the device for evaporating volatile substances; the projection on the body is configured to be unsnapped from the tab of the device for evaporating volatile substances to separate the refill from the device for evaporating volatile substances by pulling the refill from the device for evaporating volatile substances; and the ring-shaped flange on the neck is configured to be unsnapped from the tab of the device for evaporating volatile substances to separate the refill from the device for evaporating volatile substances by pulling the refill from the device for evaporating volatile substances.

11. A refill adapted to be releasably attached to a plurality of different devices for evaporating volatile substances that are separate from the refill, the refill comprising:
a body;
a neck on the body;
a thread on the neck, the thread having a means for attaching the refill to a first device for evaporating volatile substances that is separate from the refill;
a projection on the body, the projection having a means for attaching the refill to a second device for evaporating volatile substances that is separate from the refill; and
a ring-shaped flange on the neck, the ring-shaped flange having a means for attaching the refill to a third device for evaporating volatile substances that is separate from the refill.

12. The refill of claim 11, further comprising:
the means for attaching the refill to a first device, the means for attaching the refill to a second device and the means for attaching the refill to a third device for evaporating volatile substances are different means for attaching the refill to devices for evaporating volatile substances.

13. The refill of claim 11, further comprising:
the thread on the neck, the projection on the body and the ring-shaped flange on the neck are usable independently of each other to attach the refill to different devices for evaporating volatile substances.

14. The refill of claim 11, further comprising:
the thread on the neck is configured to be attached to a complementary thread of a first device for evaporating volatile substances to attach the refill to the first device for evaporating volatile substances by screwing the thread to the complementary thread of the first device for evaporating volatile substances;
the projection on the body is configured to be snap fit to a tab of a second device for evaporating volatile substances to attach the refill to the second device for evaporating volatile substances by pushing the refill onto the second device for evaporating volatile substances; and
the ring-shaped flange on the neck is configured to be snap fit to a tab of a third device for evaporating volatile substances to attach the refill to the third device for evaporating volatile substances by pushing the refill onto the third device for evaporating volatile substances.

15. The refill of claim 14, further comprising:
the thread on the neck is configured to be detached from the complementary thread of the first device for evaporating volatile substances by unscrewing the thread from the complementary thread of the first device for evaporating volatile substances;
the projection on the body is configured to be unsnapped from the tab of the second device for evaporating volatile substances by pulling the refill from the second device for evaporating volatile substances; and the ring-shaped flange on the neck is configured to be unsnapped from the tab of the third device for evaporating volatile substances by pulling the refill from the third device for evaporating volatile substances.

16. A refill adapted to be releasably attached to a plurality of different devices for evaporating volatile substances that are separate from the refill, the refill comprising:
a body;
a neck on the body;
a thread on the neck, the thread being means for screwing to a complementary thread on a first device for evaporating volatile substances that is separate from the refill;
a projection on the body, the projection being means for snap fitting to a tab on a second device for evaporating volatile substances that is separate from the refill; and
a ring-shaped flange on the neck, the ring-shaped flange being means for snap fitting to a tab on a third device for evaporating volatile substances that is separate from the refill.

17. The refill of claim 16, further comprising:
the first device, the second device and the third device for evaporating volatile substances are different and separate devices for evaporating volatile substances.

18. The refill of claim 16, further comprising:
independently of each other to attach the refill to three different devices for evaporating volatile substances.

19. The refill of claim 16, further comprising:
the thread on the neck is configured to be screwed to a complementary thread of the first device for evaporating volatile substances to attach the refill to the first device for evaporating volatile substances by screwing the thread to the complementary thread of the first device for evaporating volatile substances;
the projection on the body is configured to be snap fit to a tab of the second device for evaporating volatile substances to attach the refill to the second device for evaporating volatile substances by pushing the refill onto the second device for evaporating volatile substances; and
the ring-shaped flange on the neck is configured to be snap fit to a tab of the third device for evaporating volatile substances to attach the refill to the third device for evaporating volatile substances by pushing the refill onto the third device for evaporating volatile substances.

20. The refill of claim 19, further comprising:
the thread on the neck is configured to be detached from the complementary thread of the first device for evaporating volatile substances to separate the refill from the first device for evaporating volatile substances by unscrewing the thread from the complementary thread of the first device for evaporating volatile substances, second device for evaporating volatile substances to separate the refill from the second device for evaporating volatile substances by pulling the refill from the second device for evaporating volatile substances; and
the ring-shaped flange on the neck is configured to be unsnapped from the tab of the third device for evaporating volatile substances to separate the refill from the third device for evaporating volatile substances by pulling the refill from the third device for evaporating volatile substances.

* * * * *